United States Patent [19]

Wolff et al.

[11] Patent Number: 5,817,697
[45] Date of Patent: Oct. 6, 1998

[54] TRANSDERMAL PRESENTATION OF NITROGLYCERIN FOR PREVENTING UNDESIRED LABOR

[75] Inventors: Hans-Michael Wolff, Monheim; Dietrich Schacht, Cologne; Martin Feelisch, Erkrath, all of Germany; Bruce Ramsay, Herts, Great Britain; John Francis Martin, Beckenham, Great Britain; Christoph Christopher Lees; Adam Julian De Belder, both of London, Great Britain

[73] Assignee: Schwarz Pharma AG, Germany

[21] Appl. No.: 700,402

[22] PCT Filed: Feb. 22, 1995

[86] PCT No.: PCT/EP95/00654

§ 371 Date: Jul. 1, 1997

§ 102(e) Date: Jul. 1, 1997

[87] PCT Pub. No.: WO95/22964

PCT Pub. Date: Aug. 31, 1995

[30] Foreign Application Priority Data

Feb. 28, 1994 [DE] Germany .......................... 44 06 332.6

[51] Int. Cl.[6] ........................................................ A61K 31/13
[52] U.S. Cl. .............................................................. 514/645
[58] Field of Search ................................................ 514/645

[56] References Cited

FOREIGN PATENT DOCUMENTS

| 144 486 A2 | 6/1985 | European Pat. Off. . |
| 464 573 A1 | 1/1992 | European Pat. Off. . |
| 92/22292 | 5/1992 | WIPO . |

*Primary Examiner*—Raymond Henley, III
*Attorney, Agent, or Firm*—Merchant, Gould, Smith, Edell, Welter & Schmidt, P.A.

[57] ABSTRACT

The pharmaceutical use of nitroglycerin, which is also designated as glycerol trinitrate or, chemically, as 1,2,3-propanetriol trinitrate, in a transdermal application form prevents undesired labour in pregnant mammals. The pharmaceutical use prevents premature labour.

9 Claims, No Drawings

TRANSDERMAL PRESENTATION OF NITROGLYCERIN FOR PREVENTING UNDESIRED LABOR

The invention relates to the use of nitroglycerine to prevent undesired labor in mammals, in a transdermal form of application.

Nitroglycerine, also known as glycerol trinitrate (GTN), is a long-known chemical substance with manifold applications. Chemically, GTN is described as 1,2,3-propanetriol trinitrate. In particular, nitroglycerine is a valuable substance for treating coronary heart diseases. In view of this significance, many pharmaceutical formulations are now available. The galenical preparations of this substance by now include tablets, capsules, ointments, solutions, IV solutions, sprays, and patches for transdermal application.

Surprisingly, it has now been discovered that the use of nitroglycerine in a transdermal form of application prevents undesired labor in mammals.

Studies in animals and human beings have shown that it is possible to stop labor with this galenical form of preparation of nitroglycerine with the purposeful use of nitroglycerine in a given test subject.

The invention will be described in further detail below in terms of the study performed with human beings.

The study encompassed 18 pregnant women, each showing signs of premature labor. Their pregnancies were already advanced; they were already between 25 and 34 weeks pregnant. The GTN patches used were each applied instead of Ritodrin, a labor-inhibiting substance. All the pregnant subjects exhibited the following characteristics:
- their amniotic sacs had not yet broken;
- they had not had premature bleeding;
- the fetuses had no abnormalities.

The patients were given up to two GTN patches simultaneously per day, each with 10 or 10.8 mg of 1,2,3-propanetriol trinitrate. The surface area of the patch was 32 $cm^2$ when DEPONIT® 10 was used and 16 $cm^2$ when a novel GTN patch made by SCHWARZ PHARMA A.G. was used. This latter patch contains the nitroglycerine in an adhesive composition based on a cross-linked acrylate vinyl acetate copolymer.

There were no evident differences in terms of the success in use. Both patches prevented premature labor, stopped premature labor or ended irregular labor.

Tables 1 and 2 show that nitroglycerine in a transdermal galenical preparation prevents undesired premature labor in pregnant mammals.

It can be seen from the tables that labor was stopped after application of the patches. None of the patients suffered an unwanted premature birth. By dose-dependent administration of patches containing nitroglycerine until the expected date for the birth, it was possible to stop strong labor or to regulate irregular labor.

Exemplary embodiment 1

The patch is produced in the manner described in detail in exemplary embodiment 1 of European Patent Disclosure EP 0 144 486 B1.

A pharmaceutical product according to the present invention with a three-layer reservoir structure is produced as follows:

A pressure-sensitive adhesive composition containing nitroglycerine is prepared.

0.175 kg polyisobutylene (mean molecular weight from 900,000 to 1,400,000; commercial product OPPANOL® B 100), 0.157 kg solid aliphatic hydrocarbon resin (commercial product PICCOTAC CBHT), 0.157 kg hydrated rosin (commercial product ABITOL), 0.0105 kg 5% solution of nitroglycerine in a medium-chained triglyceride (commercial product MIGLYOL® 812), 1.174 kg petroleum spirit 80–110 as a solvent.

The product is applied onto a protective layer, on which aluminum is vapor-deposited on one side and which is equipped antiadhesively on both sides, in such a way that after the solvent evaporates, a layer of approximately 20 $g/m^2$ is obtained. Onto the thus-obtained pressure-sensitive adhesive layer, the first reservoir layer is applied as a coating, with a weight per unit of surface area of approximately 20 $g/m^2$.

The production of this reservoir layer is done by the application of a dispersion comprising:

0.05 kg 10% (G/G) ground mixture of nitroglycerine and lactose, 0.153 kg polyisobutylene (mean molecular weight from 900,000 to 1,400,00.0; commercial product OPPANOL® B 100), 0.137 kg solid aliphatic hydrocarbon resin (commercial product PICCOTAC CBHT), 0.137 kg hydrated rosin (commercial product ABITOL), 0.01 kg medium-chained triglyceride as a solvent (commercial product MIGLYOL® 812), 1.148 kg petroleum spirit 80–110 as a solvent.

The product is applied to an antiadhesive paper, and the dispersant is then evaporated off.

Analogously, a second reservoir layer with a weight per unit of surface area of approximately 50 $g/m^2$ is produced from:

0.6 kg 10% (G/G) ground mixture of nitroglycerine and lactose, 0.2 kg solid aliphatic hydrocarbon resin (commercial product PICCOTAC CBHT), 0.2 kg hydrated rosin (commercial product ABITOL), 0.025 kg medium-chained triglyceride as a solvent (commercial product MIGLYOL® 812), 1.876 kg petroleum spirit 80–110 as a solvent and is applied as a coating over the first reservoir layer.

In an analogous way, a third reservoir layer is produced from:

2.5 kg 10% (G/G) ground mixture of nitroglycerine and lactose, 0.657 kg polyisobutylene (mean molecular weight from 900,000 to 1,400,000; commercial product OPPANOL® B 100), 0.77 kg solid aliphatic hydrocarbon resin (commercial product PICCOTAC CBHT), 0.77 kg hydrated rosin (commercial product ABITOL), 7.507 kg petroleum spirit 80–110 as a solvent, where to attain a weight per unit of surface area of approximately 200 $g/m^2$, the application of the dispersion onto the antiadhesive paper takes place in three successive steps. The third reservoir layer thus obtained is applied as a coating over the second reservoir layer.

In an analogous way, the pressure-sensitive adhesive intermediate layer, with a weight per unit of surface area of approximately 20 $g/m^2$ is produced from:

0.179 kg polyisobutylene (mean molecular weight from 900,000 to 1,400,000; commercial product OPPANOL® B 100), 0.16 kg solid aliphatic hydrocarbon resin (commercial product PICCOTAC CBHT), 0.16 kg hydrated rosin (commercial product ABITOL), 1.167 kg petroleum spirit 80–110 as a solvent, and applied as a coating to the third reservoir layer.

After the pressure-sensitive adhesive intermediate layer is covered with an impermeable cover layer, the resultant laminate is divided into individual pieces to suit the therapeutic requirements.

The nitroglycerine patch has the following structure: It is a matrix system, comprising a multilayer medication-laden contact film, polyisobutylene, solid aliphatic hydrocarbon resin and hydrated rosin, which is covered on the outside with a polyester film. A patch of 32 $cm^2$ contains 32 mg of glycerol trinitrate. The mean release of active ingredient on the skin is 10 mg per 24 hours. The release area of the transdermal system is protected with a silicon-treated and metallized polyester film, which is removed prior to application.

Exemplary embodiment 2

The patch is made as described in detail in the exemplary embodiment, example 3, of PCT/EP 92/01169=WO 92/22292 A1.

This nitroglycerine patch has the following structure: It is a matrix system, comprising a nitroglycerine-containing adhesive composition on the basis of a cross-linked acrylate vinyl acetate copolymer, which is covered on the outside with a polyester film.

A patch 16 $cm^2$ in area contains 40 mg of glycerol trinitrate. The mean release of active ingredient on the skin is 10.8 mg per 24 hours. The release area of this transdermal system is protected with a polyester film, which is removed prior to application.

TABLE 1

| Dilation of the cervix | Length of pregnancy | Labor activity | Administration of Deposit ® 10, 10 mg GTN | Cessation of labor |
|---|---|---|---|---|
| 5 cm | 32 weeks | 2 contractions per 3 minutes | 2 times per day simultaneously | within 3 hours + |
| 4 cm | 32 weeks | 1 contraction per 3 minutes | 2 times per day simultaneously | within 3 hours + |
| 2 cm | 25 weeks | irregular | 1 time per day | within 5 hours + |

TABLE 2

| Dilation of the cervix | Length of pregnancy | Labor activity | Administration of GTN acrylate patch, 10.8 mg GTN | Cessation of labor |
|---|---|---|---|---|
| 5 cm | 32 weeks | 2 contractions per 3 minutes | 2 times per day simultaneousiy | within 3 hours + |
| 4 cm | 32 weeks | 1 contraction per 3 minutes | 2 times per day simultaneously | within 3 hours + |
| 2 cm | 25 weeks | irregular | 1 time per day | within 5 hours + |

We claim:

1. A method of preventing undesired labor in pregnant mammals comprising transdermal administration to said mammal of an effective amount of 1,2,3-propanetriol trinitrate.

2. The method of claim 1, wherein the transdermal administration is in the form of a patch.

3. The method of claim 2, wherein up to two patches per day may be administered.

4. A method of preventing premature births in pregnant mammals comprising transdermal administration to said mammal of an effective amount of 1,2,3-propanetriol trinitrate.

5. The method of claim 4, wherein the transdermal administration is in the form of a patch.

6. The method of claim 5, wherein up to two patches per day may be administered.

7. A method of regulating labor in pregnant mammals comprising transdermal administration to said mammal of an effective amount of 1,2,3-propanetriol trinitrate.

8. The method of claim 7, wherein the transdermal administration is in the form of a patch.

9. The method of claim 8, wherein up to two patches per day may be administered.

* * * * *